United States Patent [19]

Allman et al.

[11] Patent Number: 5,344,413
[45] Date of Patent: Sep. 6, 1994

[54] CATHETER HAVING A TIP CONNECTOR FOR RAPID CATHETER EXCHANGES

[75] Inventors: Robert C. Allman, Wakefield; Bryan J. White, Lowell, both of Mass.

[73] Assignee: C. R. Bard, Inc., Murray Hill, N.J.

[21] Appl. No.: 174,759

[22] Filed: Dec. 27, 1993

Related U.S. Application Data

[63] Continuation of Ser. No. 39,514, Mar. 29, 1993, abandoned, which is a continuation of Ser. No. 723,432, Jun. 28, 1991, abandoned.

[51] Int. Cl.⁵ .................................................. A61M 25/00
[52] U.S. Cl. ................................. 604/280; 604/164; 604/96; 604/93; 604/264; 604/281; 606/194; 128/772
[58] Field of Search ................ 604/93, 43, 95, 96, 604/97, 98, 99, 102, 103, 160, 161, 166, 264, 280128, 282, 164; 128/656-658, 772; 606/191, 192, 193, 194, 195, 196, 197, 198

[56] References Cited

U.S. PATENT DOCUMENTS

| | | | |
|---|---|---|---|
| 3,438,375 | 4/1969 | Ericson | 604/98 |
| 4,276,874 | 7/1981 | Wolvek et al. | 600/18 |
| 4,547,192 | 10/1985 | Brodsky et al. | 604/282 |
| 4,723,936 | 2/1988 | Buchbinder et al. | 128/657 |
| 4,737,153 | 4/1988 | Shimamura et al. | 604/282 |
| 4,762,130 | 8/1988 | Fogarty et al. | 604/96 |
| 4,776,347 | 10/1988 | Matthews | 604/99 |
| 4,798,193 | 1/1989 | Giesy et al. | |
| 4,886,500 | 12/1989 | Lazarus | 128/657 |
| 4,917,666 | 4/1990 | Solar et al. | 604/96 |
| 4,921,479 | 5/1990 | Grayzel | 604/280 |
| 4,921,483 | 5/1990 | Wijay et al. | 604/96 |
| 4,944,745 | 7/1990 | Sogard et al. | 604/103 |
| 4,952,357 | 8/1990 | Euteneuer | 604/96 |
| 5,032,113 | 7/1991 | Burns | 604/280 |
| 5,042,985 | 8/1991 | Elliott et al. | 606/192 |
| 5,066,298 | 11/1991 | Hess | 606/194 |
| 5,069,674 | 12/1991 | Fearnot et al. | 604/282 |
| 5,125,895 | 6/1992 | Buchbinder et al. | 604/96 |
| 5,139,511 | 8/1992 | Gill et al. | 606/198 |
| 5,211,654 | 5/1993 | Kaltenbach | 606/191 |

*Primary Examiner*—C. Fred Rosenbaum
*Assistant Examiner*—Ronald K. Stright, Jr.
*Attorney, Agent, or Firm*—Wolf, Greenfield & Sacks

[57] ABSTRACT

A catheter, such as an angioplasty catheter is provided with a distal tip segment having a helical slit. The helical slit has a proximal end and a distal end that extends fully to and intersects the rim of the tip segment that defines the distal outlet orifice. The helically slit tip segment can be unrolled partly or fully from its helical configuration and may be attached directly to an indwelling guidewire at any location along the exposed length of the guidewire. The catheter includes a guidewire lumen thereby enabling the catheter to be placed on a guidewire in conventional or in monorail fashion. Additionally, when placed on a guidewire in monorail fashion, the guidewire lumen of the catheter may be used to infuse liquids, take pressure measurements or the like.

7 Claims, 2 Drawing Sheets

CATHETER HAVING A TIP CONNECTOR FOR RAPID CATHETER EXCHANGES

This application is a continuation, of application Ser. No. 08/039,514, filed Mar. 29, 1993, now abandoned, which is a continuation of application Ser. No. 07/723,432, filed Jun. 28, 1991, now abandoned.

FIELD OF THE INVENTION

This invention relates to catheters used in medical procedures in which a guidewire is used to direct the catheter to an intended target site in the human body.

BACKGROUND OF THE INVENTION

Catheterization is a medical procedure in which a long, flexible tubular catheter is advanced into and through a passage (lumen) in the human body to place an end of the catheter at a selected target site within the body. The catheter is adapted to perform a specific procedure once it has reached the target site. Many catheterization procedures involve the use of a thin, flexible guidewire which is first placed in the patient and is manipulated and advanced to the target site. Once the guidewire is in place, the physician then may advance the catheter over and along the guidewire so that the guidewire can guide the catheter to the intended site. The catheter typically is provided with a lumen that receives the guidewire.

In some catheterization procedures, it may become necessary to change catheters during the procedure. One type of procedure in which it is common to make a catheter exchange is in percutaneous transluminal angioplasty (PTA) and percutaneous transluminal coronary angioplasty (PTCA). These angioplasty procedures typically involve the use of a catheter having an inflatable balloon at its distal end. The balloon is relatively inelastic and is inflatable to a predetermined size. The object of the angioplasty procedure is to widen the flow passage in the patient's artery, which may have become obstructed with a atherosclerotic plaque. In the angioplasty procedure, the physician manipulates the balloon catheter to place the balloon, while in a deflated condition, in the arterial obstruction (stenosis). Then the balloon is inflated under substantial pressure to forcibly dilate the region of the stenosis. A balloon angioplasty catheter typically has an elongate flexible shaft having a proximal end (outside the patient) and a distal end (inside the patient). A balloon is mounted to the distal end of the catheter shaft. Two lumens (passageways) extend through the catheter shaft. One lumen communicates with the interior of the balloon to inflate and deflate the balloon. The other lumen extends all the way through the catheter shaft and is open at the distal tip of the catheter shaft, beyond the balloon, such lumen serving to receive the guidewire. The guidewire lumen also can be used to measure the blood pressure in the patient's artery as well as to inject radiopaque contrast liquid into the artery so that the anatomy of the artery may be visualized under X-ray fluoroscopy. The physician may wish to remove the guidewire from the guidewire lumen while making such pressure measurements or injecting the radiopaque contrast liquid in order to have a larger fluid flow area through the lumen.

It may become necessary during the angioplasty procedure to exchange the indwelling catheter for another catheter. For example, a catheter exchange may be indicated when the balloon has dilated the stenosis to the full diameter of the balloon and when it is desired to still further dilate the stenosis with a larger diameter balloon. The indwelling catheter may be exchanged for a catheter having a larger balloon. A catheter exchange also may be indicated in those situations where the stenosis is so tight that the physician cannot advance the deflated balloon into the stenosis. Under those circumstances, the physician may wish to exchange the catheter for one having a smaller balloon, or a balloon specially constructed to have a lower profile (smaller effective diameter) when deflated.

Among the devices used to facilitate catheter exchanges is to modify the catheter to shorten the guidewire lumen so that it does not extend the full length of the catheter. A catheter having such a shortened guidewire lumen may be advanced along and be guided by the guidewire in monorail fashion. As will be appreciated by those skilled in the art, a monorail type of catheter facilitates catheter exchanges in that, because the guidewire lumen is short, it will not completely cover the exposed proximal end of the guidewire during the catheter exchange. Consequently, it is unnecessary to use long exchange wires or extendable guidewires. A significant disadvantage, however, of the monorail type of catheter is that by shortening the guidewire lumen, the catheter loses its capability to inject radiopaque contrast liquid or make pressure measurements, because the guidewire lumen does not extend fully to and is not accessible at the exposed proximal end of the catheter.

It would be desirable, therefore, to provide a monorail catheter in which the catheter also has the capability of making pressure measurements and injecting radiopaque contrast liquid.

SUMMARY OF THE INVENTION

The catheter embodying the invention includes an elongate flexible catheter shaft having a balloon mounted at its distal end and two lumens extending through the shaft. One of the lumens is in communication with the interior of the balloon for inflating and deflating the balloon. The other lumen extends fully through the shaft, from the proximal (accessible to the physician) to the distal tip of the shaft, and is open at an orifice at the distal tip. The portion of the shaft that extends beyond the balloon, and which defines the distal end of the guidewire lumen has a free distal end, that is, it is provided with a helical slit that extends fully to the distal end of the tip segment. The helical slit enables the tip segment to be separated along the slit and permits the helically slit portion to be wrapped about a guidewire at any location along the length of the guidewire. Thus, the distal tip segment of the shaft defines a short lumen receptive to a guidewire and by which the catheter can be guided along the guidewire in monorail fashion. The catheter so configured can be used either in a conventional mode, in which the guidewire extends through the full guidewire lumen along the full length of the catheter shaft or, alternately, can be used in a monorail fashion in which the guidewire lumen extending through most of the shaft is opened and is available for pressure monitoring or dye injection.

It is among the general objects of the invention to provide an improved catheter adapted for use with a guidewire in which the catheter can be mounted on the guidewire in monorail fashion, yet, in which the catheter maintains an open lumen extending the full length of the catheter to which pressure measurements may be made and through which radiopaque contrast liquid may be injected.

A further object of the invention is to provide a catheter of the type described in which the distal tip of the catheter is provided with a monorail segment by which the catheter may be attached to the guidewire.

Another object of the invention is to provide a catheter of the type described in which the distal tip of the catheter may be attached, in monorail fashion, to a guidewire at any location along the length of the guidewire.

A further object of the invention is to provide a catheter of the type described in which the distal tip of the catheter is provided with a segment having a helical slit that intersects, at its distal end, the distal outlet orifice of the catheter.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 1:
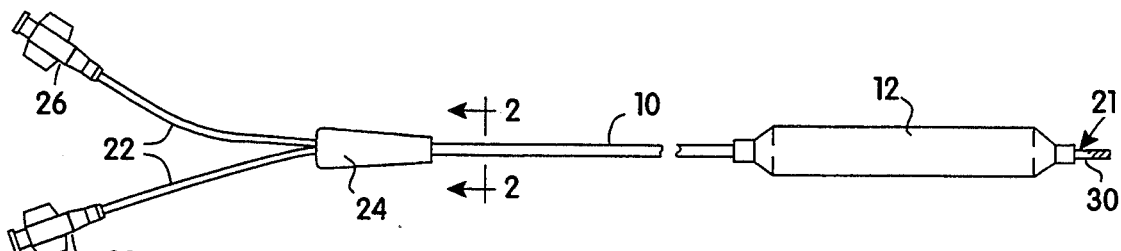
FIG. 1 is a fragmented illustration of a balloon dilatation catheter embodying the invention.

FIG. 1 illustrates a balloon dilatation catheter that may be used in angioplasty and which incorporates the invention. The catheter includes an elongate flexible shaft 10 that may be formed from a suitable polymeric material such as polyethylene. A balloon 12 suitable for use in performing angioplasty is mounted to the distal end of the shaft 10. In the illustrative embodiment, the balloon is formed as a separate element and is attached to the shaft by an appropriate adhesive, such as cyanoacrylate adhesive, as will be appreciated by those familiar with the art. The balloon may be made of polyethylene terephthalate as described, for example, in U.S. Pat. No. 4,490,421 (Levy) to which reference is made and which is hereby incorporated by reference in its entirety.

Figure 2:
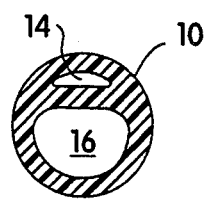
FIG. 2 is an enlarged cross-sectional illustration of the catheter shaft as seen along the line 2—2 of FIG. 1.
Figure 3:
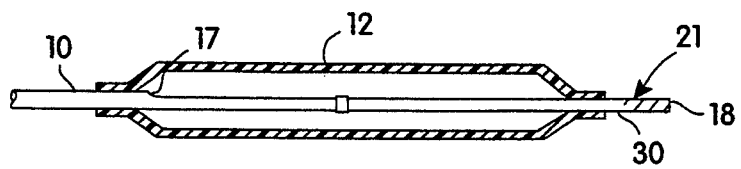
FIG. 3 is an enlarged longitudinal, partially sectional illustration of the distal portion of the catheter including the region of the balloon and distal tip.
Figure 3A:
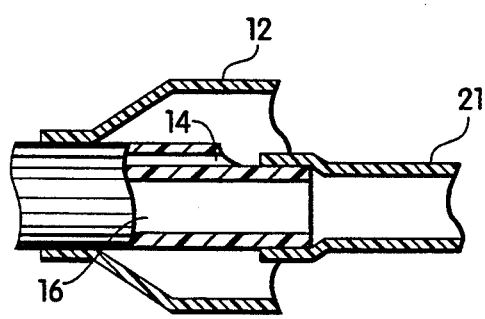
FIG. 3A is an enlarged sectional illustration of the type of construction that may be incorporated at the juncture of the tip tube of the catheter shaft with the more proximal portion of the catheter shaft.
Figure 4:
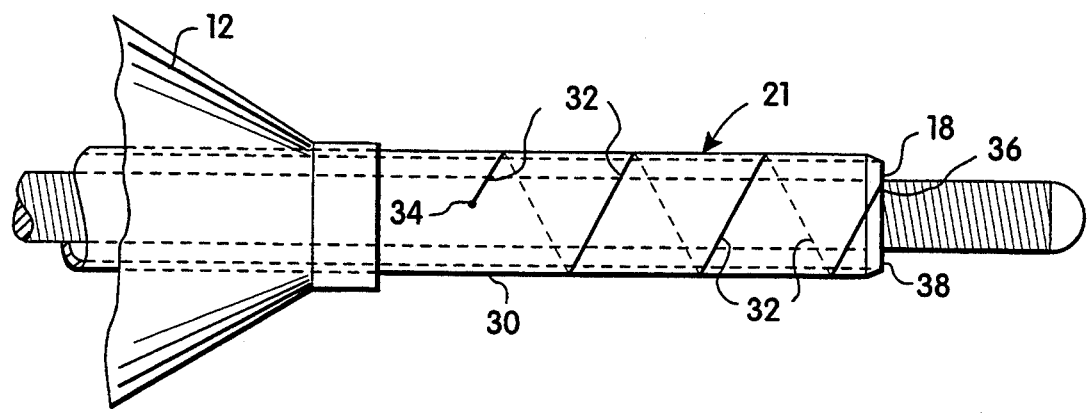
FIG. 4 is an enlarged illustration of the distal tip portion of the catheter with a guidewire extending through the catheter and the distal tip in conventional fashion.

As shown in FIG. 2, the shaft 10 of the catheter in the illustrative embodiment is formed to include two lumens, including an inflation lumen 14 and a guidewire lumen 16. The shaft may be formed as a two-lumen extrusion. The inflation lumen terminates at its distal end at a port 17 in communication with the interior of the balloon 12 to enable the balloon to be inflated and deflated. The guidewire lumen 16 extends fully through the shaft, including a tip tube 21 that defines a distal continuation of the shaft and extends through the balloon. The tip tube 21 terminates at a distal tip beyond the balloon, at an outlet orifice 18. The tip tube 21 preferably is formed from high density polyethylene and, for example, may have an inner diameter of about 0.016" and a wall thickness of about 0.005". Alternately, the tip may be formed from polyimide tubing. It may be noted that the distal end of the portion of the shaft, where it joins the tip tube 21 is formed to make a gradual transition from the D-shaped cross-section of the lumen to a circular shape so as to join smoothly with the tip tube 21 as illustrated in FIG. 3A. The inner diameter of the tip tube is large enough to provide clearance about a guidewire.

The lumens 14, 16 are accessed by the physician at the proximal end of the catheter by a pair of "pigtail" tubes 22, which are connected within a molded fitting 24 to the inflation lumen 14 and guidewire lumen 16, respectively. A conventional luer fitting 26, 28 may be attached to the proximal ends of the pigtail tubes 22.

Figure 5:
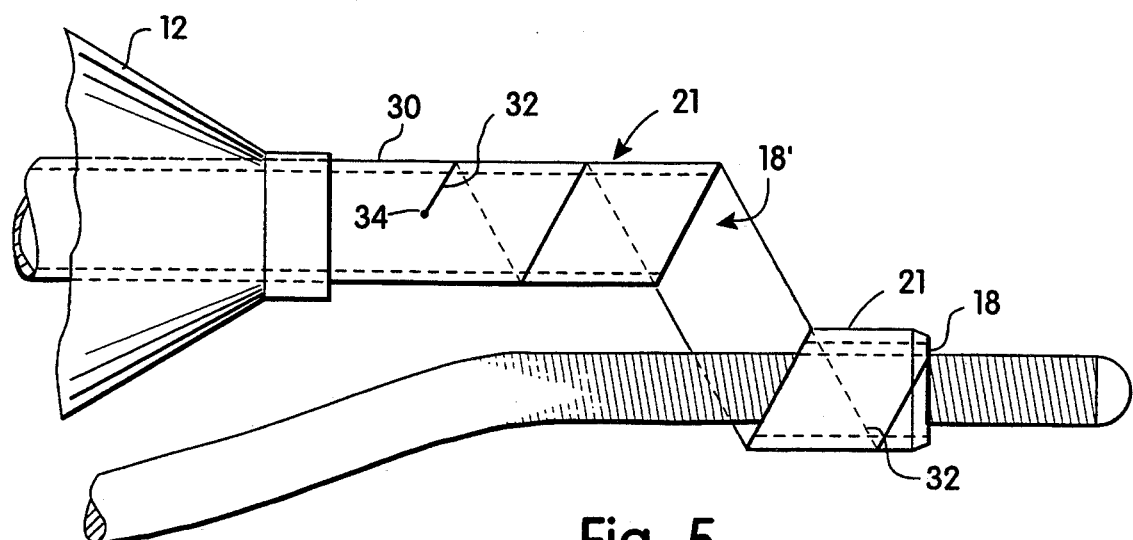
FIG. 5 is a greatly enlarged illustration of the distal tip of the catheter embodying the invention in which the tip segment is attached to a guidewire in monorail fashion.

The portion of the tip tube 21 of the shaft that extends distally beyond the distal end of the balloon defines a shaft tip segment 30. In accordance with the invention, the shaft tip segment is provided with a helical slit 32 having a proximal end 34 that terminates distally of the balloon and a distal end 36 that extends fully to and intersects the rim 38 of the tip segment 30 that defines the distal outlet orifice 18. Thus, it will be appreciated that the helically slit tip segment defines a free distal end, in that it can be unrolled partly or fully to from its helical configuration. The tip segment, so constructed, thus may be attached directly to an indwelling guidewire at any location along the exposed length of the guidewire by inserting the guidewire into the slit, unrolling the remaining distal portion of the tip segment then permitting the portion of the strip distal of the intersection of the guidewire to be wrapped about the guidewire. A guidewire so engaged with the catheter is illustrated in FIG. 5 from which it will be appreciated that the catheter then is attached to and can be advanced along the guidewire in monorail fashion. When the catheter is attached to a guidewire in monorail fashion, the distal outlet of the central lumen is disposed more proximally along the tip segment as suggested at 18'. The catheter thus maintains is ability to inject radiopaque contrast liquid into the artery and to take pressure measurements while functioning as a monorail device.

The catheter also may be used in a conventional fashion in which the guidewire extends fully through the catheter shaft, from the luer fitting 22 at the proximal end of the catheter through the continuation of the guidewire lumen in the tip segment, exiting at the distal outlet orifice 18.

From the foregoing, it will be appreciated that the invention provides an improved catheter construction in which the catheter may be advanced along a guidewire either in a conventional fashion or in a monorail fashion. The capability of operating in the monorail mode, however, does not impair the ability of the catheter to make pressure measurements and infuse radiopaque contrast liquid into the patients arteries. Additionally, the configuration to enable the catheter to be attached to the guidewire in any location along the exposed length of the guidewire.

It should be understood, however, that the foregoing description of the invention is intended to be merely illustrative thereof and that other modifications, embodiments, and equivalents may be apparent to those skilled without departing from its spirit.

Having thus described the invention, what I desire to claim and secure by Letters Patent is:

1. A cardiovascular catheter comprising:

an elongate flexible shaft having proximal and distal ends, the shaft having a primary lumen adapted to receive a guidewire;

a tubular tip segment at the distal end of the shaft, the tip segment normally being in a first configuration in communication with the primary lumen and having a distal outlet orifice, the tip segment comprising a helically coiled element and having a second configuration in which the tip segment is uncoiled to define a relatively short secondary lumen that is out of communication with the primary lumen, the secondary lumen being adapted to receive a guidewire, whereby the secondary lumen may be coupled to a guidewire while the first lumen remains unobstructed to provide communication between the proximal and distal ends of the catheter while the catheter is in engagement with a guidewire.

2. A catheter as defined in claim 1 wherein the helical element comprises a strip of polymeric material, the strip being sufficiently flexible and resilient to enable it to be uncoiled to define the short lumen and to return to the fully coiled configuration in communication with the primary lumen when released.

3. A catheter as defined in claim 2 wherein the polymeric material comprises a high density polyethylene.

4. A catheter as defined in claim 2 wherein the polymeric material comprises a polyimide.

5. A catheter as defined in claim 2 wherein the catheter has a balloon mounted on its distal end proximally of the tip segment and an inflation lumen extending from the proximal end of the catheter and having a distal end in communication with the interior of the balloon.

6. A catheter as defined in claim 1 wherein the catheter has a balloon mounted on its distal end proximally of the tip segment and an inflation lumen extending from the proximal end of the catheter and having a distal end in communication with the interior of the balloon.

7. A cardiovascular catheter comprising:

an elongate flexible shaft having proximal and distal ends, the shaft having a primary lumen adapted to receive a guidewire;

a tubular tip segment at the distal end of the shaft, the tip segment having a first configuration in communication with the primary lumen, the tip terminating in a distal outlet orifice; and a helical slit formed in the tip segment, the distal end of the helical slit extending fully to the outlet orifice thereby to define a helically coiled tip, the tip having a second configuration in which the tip segment is uncoiled to define a relatively short secondary lumen that is out of communication with the primary lumen, the secondary lumen being adapted to receive a guidewire, whereby the secondary lumen may be coupled to a guidewire while the first lumen remains unobstructed to provide communication between the proximal and distal ends of the catheter while the catheter is in engagement with a guidewire.

* * * * *